United States Patent [19]

Spencer

[11] Patent Number: 4,800,761
[45] Date of Patent: Jan. 31, 1989

[54] SAMPLE EXTRACTION SYSTEM

[76] Inventor: R. Wilson Spencer, P.O. Box 22586, Houston, Tex. 77227

[21] Appl. No.: 55,720

[22] Filed: May 29, 1987

[51] Int. Cl.⁴ .............................................. G01N 1/14
[52] U.S. Cl. .................................................. 73/863.71
[58] Field of Search ........... 73/864.63, 863.71, 863.72, 73/863.31, 863.02, 864.33, 863.41, 863.51, 863.52, 863.61, 863.34

[56] References Cited

U.S. PATENT DOCUMENTS

| | | | |
|---|---|---|---|
| 2,475,857 | 7/1949 | Reinert | 73/422 |
| 3,282,113 | 11/1966 | Sachnik | 73/422 |
| 3,681,997 | 8/1972 | Allen et al. | 73/863.61 |
| 3,950,136 | 4/1976 | Bellinga | 73/422 |
| 3,974,697 | 8/1976 | Speth | 73/863.61 |
| 4,037,475 | 7/1977 | Topham | 73/422 |
| 4,118,987 | 10/1978 | Zeh | 73/863.61 |
| 4,134,289 | 1/1979 | Bohl et al. | 73/864.34 |
| 4,207,450 | 6/1980 | Mittleman | 250/343 |
| 4,268,268 | 5/1981 | Blum | 23/250 |
| 4,272,247 | 6/1981 | Strain et al. | 23/230 |
| 4,307,620 | 12/1981 | Jiskoot | 73/863.61 |
| 4,562,747 | 1/1986 | Jaeger | 73/863.54 |
| 4,712,434 | 12/1987 | Herwig et al. | 73/864.63 |

Primary Examiner—Stewart J. Levy
Assistant Examiner—Robert R. Raevis
Attorney, Agent, or Firm—Robert C. Tucker; William David Kiesel; Timothy J. Monahan

[57] ABSTRACT

A sample extraction system is provided, comprising a block fitting including an inlet, an outlet, an interior passagway providing communication between the inlet and the outlet thereby allowing flow through the block fitting, a venturi section positioned in the interior passageway, a sample port, a sample passageway connecting the interior passageway and the sample port between the inlet and the venturi section, a re-entry port, and a re-entry passageway connecting the re-entry port and the venturi section; a loop entry line, connected on one end to a main flow line, and on the other end to the inlet of the block fitting; a loop exit line, connected on one end to the main flow line, and on the other end to the outlet of the block fitting; a sample container, having an inlet and an outlet; a sample inlet line, connected on one end to the sample port, and on the other end to the inlet of the sample container; at least one sample inlet valve, positioned in the sample inlet line; a sample exit line, connected on one end to the outlet of the sample container, and on the other end to the re-entry port; and at least one sample exit valve, positioned in the sample exit line.

9 Claims, 3 Drawing Sheets

SAMPLE EXTRACTION SYSTEM

BACKGROUND OF THE INVENTION

1. Field of the Invention

This invention relates generally to devices for sampling flowing fluids and, more particularly, to such devices which operate within a closed loop system.

2. Prior Art

In industrial chemical plants, as well as other industrial process operations, it is often necessary to obtain samples of fluids flowing in pipelines or various other types of vessels. Often, such fluids are of a hazardous nature, requiring that exposure of personnel to the sample be minimized or eliminated. In most applications where a sample is taken from a line flowing under pressure, samples are taken in sample cylinders. Such cylinders are well-known in the art. A typical cylinder is usually provided with a valve on either end, allowing a sample to be encased therein.

Various methods have been attempted in the art to safely force the sample into the cylinder. One method is to simply connect one end of the cylinder to the line containing the fluid, open the valve at the connected end and bleed the other end of the cylinder using the opposite valve until the cylinder is full of sample and entrained gases are displaced. This method obviously has its limitations with hazardous materials, since the bleeding step offers the possibility of exposing sampling personnel to the sample (a clear violation of current federal regulations). Other methods create a vacuum in the cylinder; elaborate means such as mercury or water displacement are also used. All of the prior art methods are prone to failure as well as exposure of sampling personnel to the sample. Further, these methods do not always result in a representative sample being contained in the cylinder or other sample container.

Stringent environmental regulations have resulted from an increasing concern over the safety of sampling personnel as well as exposure or discharge of hazardous materials to the atmosphere. Regulatory and safety concerns have thus severely limited sampling, resulting in elaborate and expensive containment schemes. Nevertheless, monitoring of industrial processes must still take place. The prior art devices have not managed to economically provide the necessary safety while maintaining the integrity of the sample.

SUMMARY OF THE INVENTION

Therefore, it is an object of this invention to provide a sample extraction system which minimizes exposure of sampling personnel to the sample.

It is another object of this invention to provide a sample extraction system which will economically obtain a representative sample and maintain maximum safety.

It is still another object of this invention to provide a sample extraction system which will not utilize significant external power to take a sample.

It is still another object of this invention to provide a sample extraction system which will return excess sample and entrained gases back into the source from which the sample came.

It is yet a further object of this invention to provide a sample extraction system which will accomplish all of the above objectives.

Accordingly, a sample extraction system is provided, comprising a block fitting including an inlet, an outlet, an interior passageway providing communication between the inlet and the outlet thereby allowing flow through the block fitting, a venturi section positioned in the interior passageway, a sample port, a sample passageway connecting the interior passageway and the sample port between the inlet and the venturi section, a re-entry port, and a re-entry passageway connecting the re-entry port and the venturi section; a loop entry line, connected on one end to a main flow line, and on the other end to the inlet of the block fitting; a loop exit line, connected on one end to the main flow line, and on the other end to the outlet of the block fitting; a sample container, having an inlet and an outlet; a sample inlet line, connected on one end to the sample port, and on the other end to the inlet of the sample container; at least one sample inlet valve, positioned in the sample inlet line; a sample exit line, connected on one end to the outlet of the sample container, and on the other end to the re-entry port; and at least one sample exit valve, positioned in the sample exit line.

DETAILED DESCRIPTION OF PREFERRED EMBODIMENTS OF THE INVENTION

Figure 1:
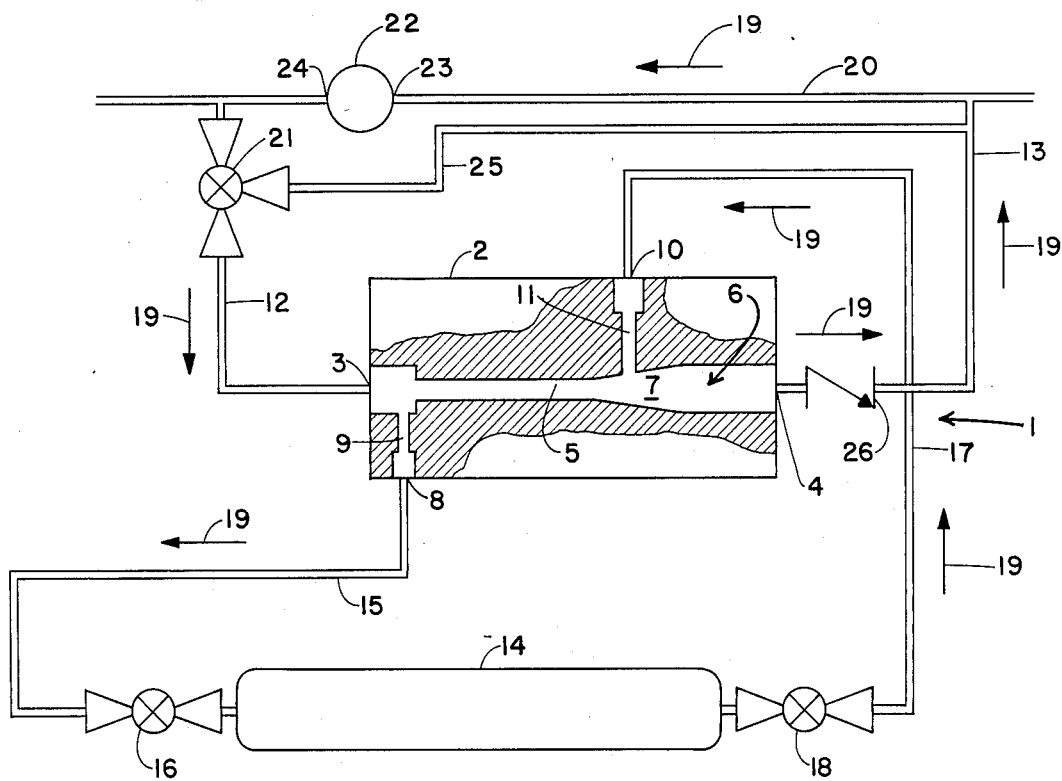
FIG. 1 is a side view of the invention with portions of the block fitting of the invention removed to sectionally reveal the interior components of the fitting.

The sample extraction system 1 is shown in FIG. 1 connected to a main flow line 20, from which a sample of flowing fluid is extracted utilizing the system 1. The system 1 utilizes the pressure differential in main flow line 20 to inject a sample of the flowing fluid into a sample container 14, usually a sample cylinder. Pressure differential may be created in a number of ways. Typically the invention may be attached to main flow line 20 on either side of an existing pressure differential caused by devices such as a pump 22 having suction port 23 and discharge port 24. Pressure differential may also be induced by devices such as an orifice plate (not shown).

As shown, the sample will flow from main flow line 20 on the discharge side of pump 22 through loop entry line 12 and into block fitting 2 at block fitting inlet 3. Flow (shown by arrows 19) is directed through block fitting interior passageway 5, exiting outlet 4 and re-entering main flow line 20 through loop exit line 13, which is connected to main flow line 20 on the suction side of pump 22. Thus, a constant flow is established through block fitting 2. When sample loop valve 21 is utilized in the three-way embodiment shown, flow may be diverted through by-pass line 25 (by-passing block fitting 2) and back into main flow line 20 either directly or through loop exit line 13 as shown. Check valve 26 prevents backflow into block fitting 2 through outlet 4.

Figure 4:
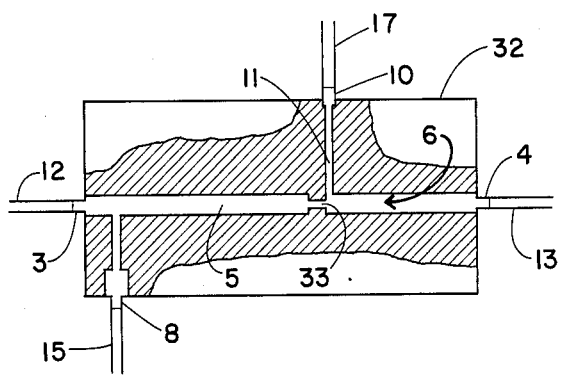
FIG. 4 is a side view of an alternate block fitting of the invention with portions removed to sectionally reveal the interior components of the fitting.

Samples are drawn from block fitting 2 utilizing the pressure differential created by pressure reducing means 6, positioned within interior passageway 5. It is preferable that pressure reducing means 6 take the form of venturi section 7 as shown. An alternate block fitting 32 is shown in FIG. 4, embodying an orifice 33 as pressure reducing means 6. As can be seen, by opening sample inlet valve 16 and sample exit valve 18, flow is established through sample passageway 9 in fitting 2, through sample port 8, sample inlet line 15, sample container 14, sample exit line 17, re-entry port 10, re-entry passageway 11, and into venturi section 7. In the embodiment shown in FIG. 4, re-entry passageway 11 should enter interior passageway 5 just downstream of orifice 33. Valves 16 and 18 should remain open until flow is established, assuring a representative sample. Sample retention is accomplished by then closing valves 16 and 18. The sample container 14 (preferably a sample cylinder) may then be removed. Displaced gases and excess sample are thus returned to the main flow line by the system 1, resulting in little or no exposure of the sample to sampling personnel or the atmosphere.

The unique block fitting 2 (shown in partial section) is preferably unitary, and can be constructed by boring a block of material (preferably stainless steel) to form the various components described above. Thus the entire sampling process is performed by simply attaching the various lines, valves and block fitting 2 as shown to sample container 14 and main flow line 20. It should be here understood that the various lines shown may be of various lengths so as to accomplish sampling in particular locations. For example sample inlet line 15 may be very short, allowing a virtually direct connection between sample inlet valve 16 and sample port 8. Sample container 14 may then be oriented vertically with sample exit valve 18 on the top and block fitting 2 on the bottom to encourage purging of entrained gases from container 14. The rate of sampling may also be varied using valves 16, 18 and 21.

Figure 2:
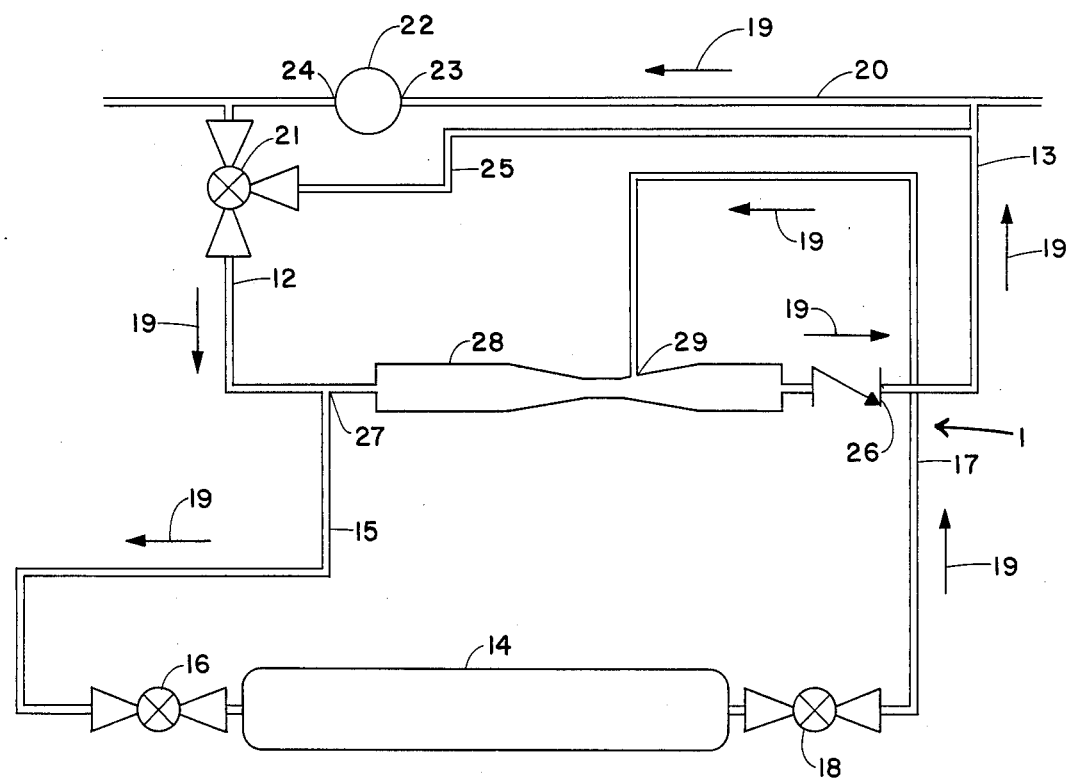
FIG. 2 is a side view of another embodiment of the invention utilizing standard fittings instead of the block fitting shown in FIG. 1.
Figure 3:
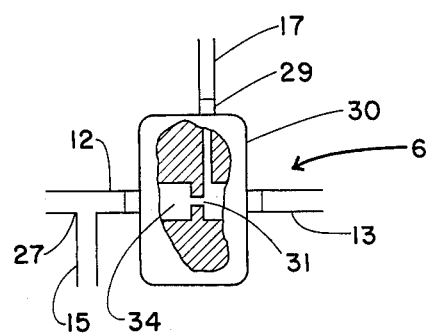
FIG. 3 is a side view of an alternate pressure reducing fitting of the invention with portions removed to sectionally reveal the interior components of the fitting.

FIG. 2 shows an alternate embodiment of the invention, wherein block fitting 2 is eliminated by inserting standard component fittings. As shown sample inlet line 15 is directly connected to loop entry line 12 by conventional means, such as tee connection 27. Just downstream from tee 27 is pressure reducing means 6, such as a venturi fitting 28 or an orifice fitting 30 (shown in FIG. 3), connected to loop entry line 12. Venturi fitting 28 (or orifice fitting 30) is provided with a re-entry port 29, to which sample exit line 17 is attached. In the case of orifice fitting 30, re-entry port 29 should extend to a point in orifice passageway 34 just downstream of the orifice 31. The utilization of component parts rather than block fitting 2 allows for custom configurations where space restrictions are a problem. It is preferable, however, that block fitting 2 be utilized wherever possible to maximize the strength and compactness of the system 1.

As can be seen, the sample extraction system disclosed herein provides a safe and efficient means for sample extraction while preserving sample integrity. Many other embodiments of the invention will occur to those skilled in the art, and are intended to be included within the scope and spirit of the following claims.

I claim:

1. A sample extraction system, comprising:
a. a block fitting, including:
  i. an inlet;
  ii. an outlet;
  iii. an interior passageway, providing communication between said inlet and said outlet thereby allowing fluid to flow through said block fitting;
  iv. a pressure reducing means, for causing a pressure drop within said interior passageway, positioned within said interior passageway;
  v. a sample port;
  vi. a sample passageway, connecting said interior passageway and said sample port between said inlet and said pressure reducing means;
  vii. a re-entry port; and
  viii. a re-entry passageway, connecting said re-entry port and said pressure reducing means;
b. a loop entry line, connected at a first point a main flow line, and on the other end to said inlet of said block fitting;
c. a loop exit line, connected on one end to said main flow line at a second point where pressure is less than that at said first point where said loop entry line is connected to said main flow line such that fluid will flow from said main flow line into said loop entry line, and on the other end to said outlet of said block fitting;
d. a sample container, having an inlet and an outlet;
e. a sample inlet line, connected on one end to said sample port, and on the other end to said inlet of said sample container;
f. at least one sample inlet valve, positioned in said sample inlet line;
g. a sample exit line, connected on one end to said outlet of said sample container, and on the other end to said re-entry port; and
h. at least one sample exit valve, positioned in said sample exit line, whereby fluid flow is induced through the loop entry line, block fitting, loop exit line, sample inlet line, container, and sample exit line due to the pressure differential between the two points only.

2. A sample extraction system according to claim 1, further comprising a sample loop valve, positioned in said loop entry line.

3. A sample extraction system according to claim 2, further comprising a bypass line, connected between said sample loop valve is a three-way valve.

4. A sample extraction system according to claim 1, wherein said pressure reducing means comprises a venturi section.

5. A sample extraction system according to claim 1, wherein said block fitting is integrally formed from a single block of material.

6. A sample extraction system according to claim 1, wherein said pressure reducing means comprises an orifice.

7. A sample extraction system, comprising:
a. a pressure reducing means, for causing a pressure drop, said pressure reducing means having an inlet and an outlet;
b. a loop entry line, connected at a first point to a main flow line, and on the other end to said inlet of said pressure reducing means;
c. a loop line, connected on one end to said main flow line, at a second point where pressure is less than that at said first point point where said loop entry line is connected to said main flow line, such that fluid will flow from said main flow line into said loop entry line, and on the other end to said outlet of said pressure reducing means;
d. a sample container, having an inlet and an outlet;
e. a sample inlet line, connected on one end to said loop entry line at a point upstream from said pressure reducing means, and on the other end to said inlet of said sample container;

f. at least one sample inlet valve, positioned in said sample inlet line;
g. a sample exit line, connected on one end to said outlet of said sample container, and on the other end to said pressure reducing means so as to fluidly communicate with the interior of said pressure reducing means at a point where pressure is reduced;
h. at least one sample exit valve, positioned in said sample exit line, whereby fluid flow is induced through the loop entry line, pressure reducing means, loop exit line, sample inlet line, container, and sample exit line due to the pressure differential between the two points only.

8. A sample extraction system according to claim 7, wherein said pressure reducing means comprises an orifice fitting.

9. A sample extraction system according to claim 7, wherein said pressure reducing means comprises a venturi fitting.

* * * * *

UNITED STATES PATENT AND TRADEMARK OFFICE
CERTIFICATE OF CORRECTION

PATENT NO. : 4,800,761

DATED : January 31, 1989

INVENTOR(S) : R. Wilson Spencer

It is certified that error appears in the above-identified patent and that said Letters Patent is hereby corrected as shown below:

In column 4, line 40 after "said sample loop valve" and before "is a three-way valve" --and said loop exit line, and wherein said sample loop valve-- should be inserted.

Signed and Sealed this

Third Day of July, 1990

Attest:

HARRY F. MANBECK, JR.

Attesting Officer      Commissioner of Patents and Trademarks